United States Patent

Yaroshenko et al.

Patent Number: 4,746,465
Date of Patent: May 24, 1988

[54] PROCESS FOR PREPARING A SCALING INHIBITOR

[76] Inventors: Galina F. Yaroshenko, ulitsa Udaltsova, 14, kv. 120; Nina M. Dyatlova, 2 Samotechny pereulok, 4, korpus 1, kv. 4; Natalya E. Khavchenko, ulitsa Chugunnye vorota, 5, korpus 3, kv. 47; Ljudmila V. Krinitskaya, ulitsa Scherbakovskaya, 7, kv. 74, all of Moscow; Leonid T. Dytjuk, ulitsa Narodnaya, 13, kv. 51; Rafail K. Samakaev, ulitsa Chkalova, 28, kv. 70, both of Orenburg; Vladimir I. Gusev, ulitsa Ulyanovykh, 57/2, kv. 20, Kazan; Leonid I. Kutyanin, ulitsa Zoi Maresevoi, 15, kv. 21, Volgograd; Nikolai A. Dobroradnykh, ulitsa Generala Shumilova, 31, kv. 44, Volgograd; Evgeny D. Kisil, bulvar Engelsa, 10, kv. 168, Volgograd; Yakov L. Uskach, ulitsa Pisemskogo, 22, kv. 12, Volgograd; Nikolai V. Matievsky, ulitsa Bystrova, 80a, kv. 24, Volgograd, all of U.S.S.R.

[21] Appl. No.: 818,866

[22] Filed: Jan. 14, 1986

Related U.S. Application Data

[63] Continuation of Ser. No. 566,213, Dec. 28, 1983, abandoned, and a continuation of Ser. No. 542,002, Oct. 14, 1983, abandoned.

[51] Int. Cl.$^4$ ................................................ C07F 9/09
[52] U.S. Cl. ................................. 260/502.5 E; 252/82
[58] Field of Search .................... 564/15; 260/502.5 E

[56] References Cited

FOREIGN PATENT DOCUMENTS

| | | |
|---|---|---|
| 898090 | 4/1984 | Belgium . |
| 2557560 | 7/1985 | France . |
| 1479381 | 7/1977 | United Kingdom . |
| 1231061 | 5/1986 | U.S.S.R. . |

*Primary Examiner*—Anton H. Sutto
*Attorney, Agent, or Firm*—Ladas & Parry

[57] ABSTRACT

The present invention relates to a process for preparing a scaling inhibitor. The process comprises reacting 1,3-diaminopropanol-2 and/or polyhydroxypropylenepolyamines of the general formula:

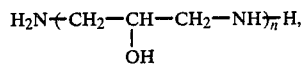

wherein n=2 to 20, with formaldehyde and phosphorus trichloride in an aqueous medium at a temperature of 35° to 50° C.; formaldehyde and phosphorus trichloride being used in amounts smaller than their stoichiometric amounts as calculated for the starting amines.

The inhibitor prepared by the process according to the present invention ensures an effective protection against scaling, e.g. of barium sulphate, calcium sulphate and calcium carbonate. The process also features a low temperature of the synthesis of the inhibitor.

3 Claims, No Drawings

PROCESS FOR PREPARING A SCALING INHIBITOR

This application is a continuation of Ser. No. 566,213, filed Dec. 28, 1983, and a continuation of Ser. No. 542,002, filed Oct. 14, 1983, both now abandoned.

FIELD OF THE INVENTION

The present invention relates to the chemistry of organophosphorus compounds and, more specifically, to processes for preparing a scaling inhibitor which can be useful in systems of water conditioning, mineral water desalination, as well as in processes of extraction, transportation and treatment of petroleum and natural gas.

BACKGROUND OF THE INVENTION

Known in the art is a process for preparing an organophosphorus compound employed as a scaling inhibitor comprising reacting polyethylenepolyamines with formaldehyde and phosphorous acid at a temperature of 100°–110° C. in hydrochloric acid (cf. USSR Inventor's Certificate No. 401692, Cl. C 08 G 33/06, 1974).

This prior art process has a disadvantage residing in that the resultant inhibitor has a low protective antiscaling effect. Furthermore, the process features a high synthesis temperature.

Also known in the art is a process for preparing a scaling inhibitor by reacting formaldehyde, phosphorous acid, a mixture of polyethylenepolyamine, monoethanolamine and carbamide, as well as ammonium chloride and/or hexamethylenetetramine in a mass ratio of 100:55–75:25–40:50–70:34–35 at a temperature of 98°–100° C. (cf. USSR Inventor's Certificate No. 719970, Cl. C 02 B 5/00).

A disadvantage of this process resides in that the thus-prepared inhibitor has a low anstiscaling effect. Moreover, the process itself has a high temperature of the synthesis.

Another prior art process for preparing a scaling inhibitor comprises reacting formaldehyde with phosphorous acid and a nitrogen-containing condensation product obtained by interaction of dischloroethane and aqueous ammonia at a temperature of from 110° to 135° C. This condensation product has the following composition, percent by mass:

| | |
|---|---|
| polyethylenepolyamine hydrochloride | 38 to 70 |
| ammonia | 0.1 to 1.0 |
| ammonium chloride | 1.0 to 6.0 |
| water | 25 to 27. |

The synthesis of the inhibitor is conducted at a temperature of 98°–100° C. in a medium of diluted hydrochloric acid, followed by alkalization of the resultant solution with sodium hydroxide to a pH of 3.6–3.9 (cf. USSR Inventor's Certificate No.726123, Cl. C 08 G 79/04).

A disadvantage of this process resides in the use of high temperatures for the synthesis. Furthermore, the thus-produced scaling inhibitor is less effective in stabilization of oversaturated solutions of mineral salts.

Still another prior art process for preparing a scaling inhibitor comprises treatment of a mixture containing amines (polyethylenepolyamine, monoethanolamine), ammonium chloride and carbamide with formaldehyde and phosphorus trichloride in an aqueous medium at a temperature of 98°–100° C., followed by distilling-off the resulting phosphorous acid from the reaction mass and neutralization of the latter with an alkali metal hydroxide (for example, sodium hydroxide) to a pH of 3.7–3.8 (cf. USSR Inventor's Certificate No. 791645, Cl. C 02 F 5/12, 1980).

A disadvantage of this process resides in the use of high temperatures for the synthesis. Furthermore, the thus-produced scaling inhibitor is but less effective against scaling, especially barium sulphate scaling.

Known in the art is a process for preparing a scaling inhibitor which comprises reacting formaldehyde, phosphorus trichloride and amines (the process of phosphonomethylation) in an aqueous medium at a temperature of 35° to 50° C. As these amines a product is used which is prepared by reacting epichlorohydrin and ammonia in the form of an aqueous solution at a temperature of 10°–15° C. and a molar ratio of the reagents of 1:5–15 respectively, followed by treatment of the reaction mass with an alkali metal hydroxide in an amount of 1.0–1.1 mol per mol of epichlorohydrin and distilling-off the unreacted ammonia with a subsequent vacuum fractionation to give a product comprising 1,3-diaminopropanol-2 and/or polyhydroxypropylenepolyamines of the general formula:

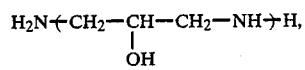

wherein n=2–5. The reaction of amines with formaldehyde and phosphorus trichloride is effected at their molar ratio of 1:4.3–4.6:3.66–4.0 (cf. British Pat. No. 1,479,381 Cl. C 07 F 9/38, C 02 B 5/06).

The inhibitor prepared by this process is less effective against scaling.

A further process known in the art for the preparation of a scaling inhibitor comprises reacting 1,3-diaminopropanol-2 and/or polyhydroxypropylenepolyamines of the general formula:

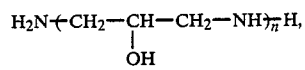

wherein n=2 to 20 with formaldehyde and phosphorus trichloride in an aqueous medium at the temperature of 45° C. and the molar ratio of amines to formaldehyde and phosphorus trichloride of 1:3.79:3.87 respectively (cf. USSR Inventor's Certificate No. 876666, Cl. C 08 G 79/04).

The inhibitor produced by this process has an insufficient protective antiscaling effect.

SUMMARY OF THE INVENTION

It is an object of the present invention to provide such a process which would make it possible to prepare a scaling inhibitor possessing a high protective effect.

It is another object of the present invention to provide such a process which would be carried out at a lower temperature.

These and other objects of the present invention are accomplished by a process for preparing a scaling inhibitor which comprises reacting 1,3-diaminopropanol-2 and/or polyhydroxypropylenepolyamines of the general formula:

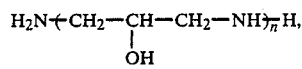

wherein n=2-20, with formaldehyde and phosphorus trichloride (the process of phosphonomethylation) in an aqueous medium at a temperature within the range of from 35° to 50° C., wherein according to the present invention, formaldehyde and phosphorus trichloride are used in smaller amounts than their stoichiometric ones as based on the starting amines.

Owing to a lowered amount of the starting reagents in respect of their stoichiometric amounts (as calculated for amines) the process according to the present invention makes it possible to produce an inhibitor with a high protective antiscaling effect. Furthermore, the process according to the present invention makes it possible to carry out the reaction of the starting products under mild conditions (at a temperature of from 35° to 50° C.).

The use of phosphonomethylation temperatures of below 35° C. causes a reduce rate of the reaction and an incomplete phosphonomethylation of the above-mentioned amines. Temperatures above 50° C. are undesirable either, since the process of phosphonomethylation is rather exothermal and it is very difficult to keep it under control at elevated temperatures.

One of embodiments of the present invention (the first embodiment) comprises a process for the preparation of a scaling inhibitor, wherein as the amines use is made of a product prepared by reacting epichlorohydrin and ammonia (in the form of an aqueous solution) at a temperature within the range of from 5° to 20° C. at a molar ratio of the reagents of 1:5-15 respectively, followed by treatment of the reaction mass with an alkali metal hydroxide in an amount of 1.0-1.1 mol per mol of epichlorohydrin and distilling-off the unreacted ammonia; the resulting product has the following composition, percent by mass:

a mixture of 1,3-diaminopropanol-2 or polyhydroxypropylenepolyamines of the general formula:

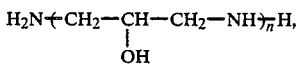

| wherein n = 2-5 | 3 to 33 |
| alkali metal chloride | 2 to 25 |
| water | the balance; | the reaction of these amines with formaldehyde and phosphorus trichloride is effected at their molar ratio of 1:2.5–3.3:2.95–3.24 respectively.

Owing to the fact that formaldehyde and phosphorus trichloride are used in smaller amounts than their stoichiometric ones as based on the starting amines, the resultant scaling inhibitor has a high protective effect. Thus, the protective effect of the scaling inhibitor prepared according to the USSR Inventor's Certificate No. 726123 is only 38.4%, the protective effect of the inhibitor of the USSR Inventor's Certificate No. 876666 is 34.3%, the protectice effect of the inhibitor of British Pat. No. 1,479,381 is 38.5–42.6%, whereas the scaling inhibitor prepared by the process according to the present invention (its first embodiment) ensures a protective effect of from 47.7 to 78.6%.

The scaling inhibitor prepared by the process according to the present invention (the first embodiment) has a low congelation temperature (down to −100° C.) which provides for the possibility of using and storing same in the Far North regions without adding antifreezes thereto.

Furthermore, the use of the starting reagents in the above-specified amounts makes it possible to prepare an inhibitor ensuring a longer protection of the oil well equipment when using it by the method of a discontinuous introduction into the productive pool. This inhibitor exhibits improved adsorption-desorption characteristics. When injected into the productive pool, the scaling inhibitor is adsorbed on the porous rock surface and gets slowly washed-away by the oil-well product. This enables a considerably smaller rate of consumption of the inhibitor (by 2–3 times) as compared to that described in British Pat. No. 1,479,381).

As it has been mentioned hereinabove, in the first embodiment of the present invention the amines are obtained by reacting epichlorohydrin and aqueous ammonia at a molar ratio of the components of 1:5-15 respectively at a temperature within the range of from 5° to 20° C. It is undesirable to use ammonia in an amount less than that specified in relation to epichlorohydrin, since there is the risk of the formation of a water-insoluble polymer with a considerable amount of the non-reactive tertiary nitrogen. The use of ammonia in an amount exceeding that specified in relation to epichlorohydrin results in non-productive expenses for the removal of the aqueous solution of ammonia during the synthesis of the inhibitor. The reaction of epichlorohydrin with ammonia in the form of an aqueous solution at a temperature below 5° C. is inexpedient, since it results in a sharp reduction of the speed of the formation of the mixture of amines (1,3-diaminopropanol-2- and polyhydroxypropylenepolyamines of the above-given general formula). Elevation of temperature above 20° C. also increases the risk of the formation of an undesirable polymeric product with a considerable amount of tertiary nitrogen.

As it has been mentioned hereinbefore, the reaction of formaldehyde, phosphorus trichloride and amines (the process of phosphonomethylation) is conducted at their molar ratio of 1:2.5-3.3:2.95-3.24 respectively.

It is inadvisable to use formaldehyde and phosphorus trichloride in an amount smaller that specified in relation to the mixture of 1,3-diaminopropanol-2 and polyhydroxypropylenepolyamines due to the formation of a scaling inhibitor exhibiting a low protective effect. For the same reason, it is also undesirable to use formaldehyde and phosphorus trichloride in an amount exceeding that mentioned hereinabove.

Another embodiment of the present invention (the second embodiment) relates to a process for preparing a scaling inhibitor, wherein as the amines use is made of 1,3-diaminopropanol-2 and/or polyhydroxypropylenepolyamines of the general formula:

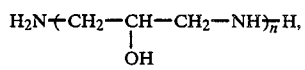

wherein n=2 to 20; the reaction of amines with formaldehyde and phosphorus trichloride is conducted at their molar ratio of 1:3.0:3.0 respectively; on completion of the reaction of these reagents hydrochloric acid contained in the reaction mass is distilled-off therefrom and the reaction mass is neutralized to a pH value of not less than 6.

Owing to the fact that formaldehyde and phosphorus trichloride are used in smaller amounts than their stoichiometric values as based on the starting amines, as well as due to the fact that hydrochloric acid is removed from the reaction mass and the latter is neutralized to a pH of not less than 6, the resultant scaling inhibitor is distinguished by a high protective effect, especially against barium sulphate scaling (in the first embodiment the protective effect against barium sulphate scaling is somewhat lower). Thus, the protective effect of the scaling inhibitor produced by the process according to the present invention (the second embodiment) is 72–79.6% and in the case of barium sulphate it can reach even 100%.

As it has been already mentioned hereinabove, the reaction of formaldehyde, phosphorus trichloride and amines (the process of phosphonomethylation) is conducted at their molar ratio of 1:3.0:3.0 respectively.

It is inexpedient to use formaldehyde and phosphorus trichloride in an amount smaller than that specified in respect of 1,3-diaminopropanol-2 or/and polyhydroxypropylenepolyamines because the resultant scaling inhibitor has a low protective effect. For the same reason, it is inadvisable to use formaldehyde and phosphorus trichloride in an amount surpassing the upper limit thereof specified hereinbefore.

The process of neutralization of the reaction mass conducted to a pH value of less than 6 results in the inhibitor having a low effect against barium sulphate scaling.

DETAILED DESCRIPTION OF THE INVENTION

The process for preparing a scaling inhibitor according to the first embodiment of the present invention is effected in the following manner.

Into an aqueous solution of ammonia epichlorohydrin is introduced at such a rate that the reaction mass temperature would not elevate above 5°–20° C. The starting reagents (epichlorohydrin and ammonia) are used in a molar ratio equal to 1:5–15 respectively. Thereafter an alkali metal hydroxide such as sodium hydroxide or potassium hydroxide is added to the reaction mass in small portions to neutralize the evolving hydrogen chloride, the molar ratio between epichlorohydrin and the alkali metal hydroxide being within the range of 1:1 to 1:1.1. Thereafter the unreacted (excessive) ammonia is distilled-off.

As a result, a product is obtained which comprises a mixture of amines and has the following composition, % by mass:

a mixture of 1,3-diaminopropanol-2 and polyhydroxypropileneamines of the general formula:

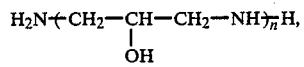

| wherein n = 2–5 | 3 to 33 |
|---|---|
| alkali metal chloride | 2 to 25 |
| water | the balance. |

The product of the above-specified composition is added with formaldehyde and phosphorus trichloride at a molar ratio of amines to formaldehyde and phosphorus trichloride of 1:2.5–3.3:2.95–3.24 respectively. On completion of the addition the reaction temperature is elevated to 35°–50° C. in the reactor and the reaction mass is maintained at this temperature for a period of from 3 to 6 hours.

The process for preparing a scaling inhibitor according to the second embodiment of the present invention is effected in the following manner.

Into an aqueous solution of 1,3-diaminopropanol-2 or/and polyhydroxypropylenepolyamines of the general formula:

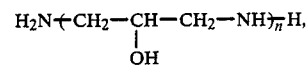

wherein n=2 to 20, formaldehyde and phosphorus trichloride are charged at the molar ratio of amines to formaldehyde and phosphorus trichloride equal to 1:3.0:3.0 respectively. As polyhydroxypropylenepolyamines use can be made of both individual amines and various mixtures thereof. Then the reaction mass temperature is elevated to 35°–50° C. and maintained for a period of 3 to 6 hours.

Thereafter hydrochloric acid is distilled-off from the reaction mass and the latter is neutralized to a pH of not less than 6 using an alkali metal hydroxide or gaseous ammonia.

The starting 1,3-diaminopropanol-2 and/or polyhydroxypropylenepolyamines of the above-given general formula employed in the second embodiment of the present invention are prepared by interaction of epichlorohydrin with an excess of ammonia employed as an aqueous solution at a temperature within the range of from 10° to 30° C. for a period of from ¼ to 6 hours, followed by neutralization of the evolved hydrogen chloride by means of an aqueous solution of an alkali, removing the unreacted ammonia and a vacuum fractionation of the reaction mass (cf. U.S. Pat. No. 3,432,553 Cl. 260-585).

For a better understanding of the present invention, some specific examples illustrating its first embodiment are given hereinbelow.

EXAMPLE 1

Into an enameled reactor provided with a reflux condenser a stirrer, cooling means, a thermometer and a pH-meter 513 kg of a 25% aqueous solution of ammonia are charged and at the temperature of 5° C. 22.6 kg of epichlorohydrin are added thereto (molar ratio between epichlorohydrin and ammonia is 1:15). Then, for neutralization of the evolving hydrogen chloride 9.77 kg of a granulated sodium hydroxide are charged into the reactor in small portions (the molar ratio of epichlorohydrin to sodium hydroxide is 1:1), whereafter the reaction mass is kept for 3 hours. Then the unreacted (excessive) ammonia is distilled-off to give 100 kg of a product having the following composition, percent by mass:

| mixture of 1,3-diaminopropanol-2 and polyhydroxypropylenepolyamines of the general formula given hereinabove (80% - n = 1; 10% - n = 2; 5% - n = 3; 3% - n = 4; 2% - n = 5) | 22 |
|---|---|
| sodium chloride | 15 |
| water | the balance. |

Thereafter, 62.4 kg of a 37% aqueous solution of formaldehyde and 100 kg of phosphorus trichloride are charged into the reactor under stirring (the molar ratio of the amines to formaldehyde and phosphorus trichloride is equal to 1:3.2:3.03 respectively). On completion of charging, temperature in the reactor is elevated to 35° C. and the reaction mass is kept at this temperature for 4 hours. As a result of the synthesis (the process of phosphonomethylation) 262 kg of the inhibitor are produced.

EXAMPLE 2

Into a reactor described in the foregoing Example 1 116.5 kg of a 10% aqueous solution of ammonia are charged and at the temperature of 20° C. 3.08 kg of epichlorohydrin are added thereto (the molar ratio of epichlorohydrin to ammonia is equal to 1:10). Thereafter, for neutralization of the evolving hydrogen chloride 1.39 kg of sodium hydroxide is fed into the reactor in small portions (the molar ratio of epichlorohydrin to sodium hydroxide is 1:1.05) and the reaction mass is maintained under these conditions for 4 hours. Then the excess of ammonia is distilled-off.

As a result, 100 kg of the product is thus obtained which has the following composition, percent by mass:

| | |
|---|---|
| a mixture of 1,3-diaminopropanol-2 and polyhydroxypropylenepolyamines of the above-given general formula (75% - n = 1, 15% - n = 2, 5% - n = 3, 3% - n = 4, 2% - n = 5) | |
| sodium chloride | 2 |
| water | the balance. |

Then 9 kg of a 35% aqueous solution of formaldehyde and 14.5 kg of phosphorus trichloride are charged into the reactor under stirring (the molar ratio of the amines to formaldehyde and phosphorus trichloride is 1:3.3:3.24 respectively). On completion of the charging, temperature in the reactor is raised to 50° C. and the reaction mass is maintained at this temperature for 6 hours. As a result of the synthesis 124 kg of the inhibitor are obtained.

EXAMPLE 3

Into a reactor described in Example 1 hereinbefore 302 kg of a 25% aqueous solution of ammonia are charged and 33.9 kg of epichlorohydrin are added thereto at the temperature of 15° C. (the molar ratio of epichlorohydrin to ammonia in 1:5). Thereafter, 19 kg of sodium hydroxide are fed into the reactor in small portions for neutralization of the evolving hydrogen chloride (the molar ratio of epichlorohydrin to sodium hydroxide is 1:1.1) and the reaction mass is maintained for 3 hours. Then the excessive amount of ammonia is distilled-off.

As a result, 100 kg of the product of the following composition are obtained, percent by mass:

| | |
|---|---|
| mixture of 1,3-diaminopropanol-2 and polyhydroxypropylenepolyamines of the above-given general formula (86% — n = 1, 12% - n = 2, 1% — n = 3, 0.75% — n = 4, 0.25% — = 5) | 33 |
| sodium chloride | 25 |
| water | the balance |

Thereafter, 85 kg of a 32% aqueous solution of formaldehyde and 142 kg of phosphorus trichloride are charged into the reactor under stirring (the molar ratio of the amines to formaldehyde and phosphorus trichloride is equal to 1:2.5:2.95 respectively). On completion of the charging temperature in the reactor is elevated to 40° C. and the reaction mass is maintained for 3 hours.

As a result of the synthesis 317 kg of the inhibitor are produced.

EXAMPLE 4

The inhibitor is prepared in a manner similar to that described in Example 1 hereinbefore. The difference resides in that potassium hydroxide is used for neutralization of hydrogen chloride evolving in the reaction of epichlorohydrin with ammonia employed as an aqueous solution.

As a result, 265 kg of the inhibitor are obtained.

EXAMPLE 5

The reaction of epichlorohydrin with ammonia employed as an aqueous solution is carried out in a manner similar to that of Example 1, but at the temperature of 15° C. The process of phosphonomethylation is conducted as described in Example 1 for 4 hours, but at the temperature of 45° C. to obtain, as a result of the synthesis, 264 kg of the inhibitor.

EXAMPLE 6

The reaction of epichlorohydrin with ammonia employed as an aqueous solution is conducted as described in Example 1, but at the temperature of 20° C. for 4 hours. The process of phosphonomethylation is carried out as described in Example 1 for 4 hours, but at the temperature of 50° C.

As a result of the synthesis 265 kg of the inhibitor are obtained.

EXAMPLE 7

The reaction of epichlorohydrin with ammonia employed as an aqueous solution is carried out as described in Example 2 hereinbefore with the only difference that the molar ratio of epichlorohydrin to ammonia is equal to 1:15 respectively.

Afterwards, 8.6 kg of a 37% aqueous solution of formaldehyde and 13.6 kg of phosphorus trichloride are charged into the reactor under stirring (the molar ratio of the amines to formaldehyde and phosphorus trichloride is equal to 1:3.27;3.02 respectively). On completion of the charging, temperature in the reactor is elevated to 40° C. and the reaction mass is maintained for 4 hours.

As a result, 122 kg of the inhibitor are obtained.

EXAMPLE 8

Epichlorohydrin is reacted with ammonia in the form of an aqueous solution following the procedure similar to that described in Example 1 hereinbefore, except that the molar ratio between epichlorohydrin and ammonia is equal to 1:10 and the reaction temperature is 20° C.

The process of phosphonomethylation is conducted as described in Example 1, but at the temperature of 40° C. for 4 hours.

As a result of the synthesis, 260 kg of the inhibitor are obtained.

EXAMPLE 9

The reaction of epichlorohydrin with ammonia employed as an aqueous solution is carried out in a manner similar to that described in Example 3, but at the temperature of 20° C. and at the molar ratio of epichlorohydrin to ammonia of 1:15.

The process of phosphonomethylation is conducted as in Example 3 at the temperature of 40° C., but for 4 hours. In doing so, 95 kg of a 37% aqueous solution of formaldehyde and 150 kg of phosphorus trichloride are charged into the reactor (the molar ratio of the amines to formaldehyde and phosphorus trichloride is equal to 1:3.25:3.03 respectively).

As a result of the synthesis, 345 kg of the inhibitor are thus obtained.

For a better understanding of the present invention, some specific examples illustrating its second embodiment are given hereinbelow.

EXAMPLE 10

Into an enameled reactor provided with a reflux condenser, means for stirring, measuring pH, temperature, as well as cooling means 31 kg of 1,3-diaminopropanol-2 and 69 kg of water are charged. Then 84 kg of a 37% aqueous solution of formaldehyde and 142 kg of phosphorus trichloride are added into the reactor under stirring (the molar ratio of the amine to formaldehyde and phosphorus trichloride is equal to 1:3.0:3.0 respectively). On completion of charging, the reaction temperature is elevated to 45° C. and the reaction mass is maintained under these conditions for 4 hours. After cooling of the reaction mass hydrochloric acid is distilled-off in the amount of 98% as calculated for hydrogen chloride (which is formed in hydrolysis of phosphorus trichloride thus contributing to the formation of an acid pH of the solution necessary for carrying out the reaction of phosphonomethylation).

On completion of the distilling-off of hydrochloric acid a 42% solution of sodium hydroxide is fed into the reaction mass in small portions to achieve the pH value of 7.5.

As a result, 436 kg of a scaling inhibitor are obtained.

EXAMPLE 11

A scaling inhibitor is prepared in a manner similar to that described in the foregoing Example 10. The difference resides in that as the amines use is made of a mixture of 1,3-diaminopropanol-2 (n=1) and polyhydroxypropyleneamines of the above-given general formula, wherein n=6-10 at the following proportions of the components in the mixture, percent by mass:

| | |
|---|---|
| n = 1 | 80 |
| n = 6-10 | 20. |

The process of phosphonomethylation is carried out at the temperature of 35° C. for 6 hours. After cooling of the reaction mass hydrochloric acid is distilled-off in the amount of 85% as calculated for hydrogen chloride. On completion of the distilling-off, a 42% solution of potassium hydroxide is fed into the reaction mass to bring its pH to 6.

As a result, 395 kg of a scaling inhibitor are thus obtained.

EXAMPLE 12

A scaling inhibitor is produced in a manner similar to that described in Example 10 hereinabove. The difference resides in that as the amines use is made of polyhydroxypropylenepolyamides of the above-given general formula, wherein n is 11 to 20.

The process of phosphonomethylation is conducted at the temperature of 50° C. for 3 hours. After cooling of the reaction mass hydrochloric acid is distilled-off in the amount of 96% as calculated for hydrogen chloride. On completion of the distilling-off gaseous ammonia is introduced into the reaction mass to bring its pH to 7.0.

As a result, 400 kg of a scaling inhibitor are thus obtained.

EXAMPLE 13

A scaling inhibitor is prepared following the procedure similar to that described in Example 10 hereinbefore. The difference resides in that as the amine use is made of polyhydroxypropylenepolyamine of the above-given general formula, wherein n=20.

The process of phosphonomethylation is conducted at the temperature of 35° C. for 4 hours. After cooling of the reaction mass hydrochloric acid is distilled-off in the amount of 85% as calculated for hydrogen chloride. On completion of distilling-off, a 42% solution of sodium hydroxide is fed into the reaction mass in small portions to bring its pH to 6.

As a result, 380 kg of a scaling inhibitor are thus obtained.

EXAMPLE 14

A scaling inhibitor is produced in a manner similar to that of Example 10. The difference resides in that as the amines use is made of a mixture of 1,3-diaminopropanol-2 (n=1) and polyhydroxypropylenepolyamines of the above-given general formula, wherein n=2 to 20 at the following proportions of the products in the mixture, percent by mass:

| | | | |
|---|---|---|---|
| n = 1 | 60 | n = 6-10 | 15 |
| n = 2-5 | 20 | n = 11-20 | 5. |

The process of phosphonomethylation is conducted at the temperature of 45° C. for 4 hours. On completion of the reaction mass hydrochloric acid is distilled-off in the amount of 90% as based on hydrogen chloride. After distillation a 42% solution of sodium hydroxide is added to the reaction mass in small portions to bring its pH to 8.0.

As a result, 460 kg of a scaling inhibitor are thus produced.

The inhibitor prepared by the process according to the present invention (the first and second embodiments thereof) was tested for the protective effect against scaling of such minerals as calcium sulphate and calcium carbonate.

The assessment of the protective effect was effected by introduction of 10 mg/l (as calculated for the mixture of phosphonomethylated amines) of the inhibitor into 750 ml of mineralized pool water.

To this end, into a stainless steel beaker 200 ml of the mineralized pool water are poured which containes the inhibitor in the amount of 10 mg/l, whereafter a portion of water is evaporated by heating. During evaporation the remaining 550 ml of the mineralized pool water treated with the inhibitor are continuously and gradually added into the beaker to maintain the working volume constant (and equal to 200 ml). In all of the experiments the evaporation ratio was 2.75. The mineralized pool water had the following properties:

| | |
|---|---|
| density, g/cm³ | 1.055 |
| total mineralization, mg-equiv/l | 2,717.596 |
| K⁺ + Na⁺, mg-equiv/l | 1,149.022 |
| $Ca^{2+}$, mg-equiv/l | 135.763 |
| $Mg^{2+}$, mg-equiv/l | 74.013 |
| $Cl^-$, mg-equiv/l | 1,277.595 |
| $SO_4^{2-}$, mg-equiv/l | 77.991 |
| $HCO_3^-$, mg-equiv/l | 0.196. |

For the purpose of comparison, the inhibitors produced by the known processes according to the USSR Inventor's Certificates Nos. 726123, 791645, 876666 and to British Pat. No. 1,479,381 were tested following the same procedure.

The efficiency of scaling inhibitors produced by the known processes and by the process according to the present invention was assessed through determination of the amount of the residue formed on the beaker's walls. A control experiment was also performed using the same testing procedure but without the addition of a scaling inhibitor into the mineralized pool water.

The protective effect of the scaling inhibitor was calculated by the formula:

$$E = \frac{A - B}{A} \times 100,$$

wherein
E—protective effect of the inhibitor, %,
A—weight of the deposited mineral salts (scale) on the beaker walls in the control experiment (without inhibitor), g,
B—weight of the scale on the beaker walls with the use of the inhibitor, g.

Shown in Table 1 are the data on the protective effect of the inhibitor produced by the process according to the present invention (Examples 1 through 14) and of the inhibitors produced by known processes disclosed in the USSR Inventor's Certificates Nos. 726123, 791645, 876666 and according to British Pat. No. 1,479,381.

TABLE 1

| Process for preparing scaling inhibitor, according to | Inhibitor concentration, | Protective effect, % |
|---|---|---|
| 1 | 2 | 3 |
| Control | — | 0 |
| USSR Inventor's Certificate No. 726123 | 10.0 | 38.4 |
| USSR Inventor's Certificate No. 791645 | " | 39.0 |
| USSR Inventor's Certificate No. 876666 | " | 41.4 |
| British Patent No. 1,479,381 | " | 42.6 |
| The present invention, first embodiment: | | |
| Example 1 | " | 69.6 |
| Example 2 | " | 47.7 |
| Example 3 | " | 69.9 |
| Example 4 | " | 70.0 |
| Example 5 | " | 62.8 |
| Example 6 | " | 70.1 |
| Example 7 | " | 48.0 |
| Example 8 | " | 64.0 |
| Example 9 | " | 78.6 |
| The present invention, second embodiment | | |
| Example 10 | " | 73.7 |
| Example 11 | " | 72.0 |
| Example 12 | " | 79.6 |
| Example 13 | " | 76.3 |

TABLE 1-continued

| Process for preparing scaling inhibitor, according to | Inhibitor concentration, | Protective effect, % |
|---|---|---|
| Example 14 | " | 75.9 |

From the data presented in Table 1 it is seen that the scaling inhibitor produced by the process according to the present invention is considerably superior over the prior art inhibitors.

The inhibitor prepared by the process according to the present invention (second embodiment) and the inhibitors prepared by the processes disclosed in the USSR Inventor's Certificates Nos. 726123, 876666 and British Pat. No. 1,479,381 were tested for the protective effect against barium sulphate scaling.

The protective effect was assessed on a model water stimulating pool waters of oil deposits causing barium sulphate scaling.

To this end, an aqueous solution oversaturated in respect of barium sulphate is prepared by mixing two solutions I and II. Characteristics of the salt composition of these solutions are shown in Table 2.

TABLE 2

| Content of salts, mg/l | | | |
|---|---|---|---|
| Solution I | | Solution II | |
| $BaCl_2.6H_2O$ | NaCl | $Na_2SO_4$ | NaCl |
| 560 | 30,000 | 800 | 30,000 |

The tests were conducted at the temperature of 80° C. under continuous stirring of the oversaturated aqueous solution. The duration of the experiments was 8 hours. The protective effect against barium sulphate scaling was determined by the gravimetric method according to the formula:

$$E = \left(1 - \frac{P}{P_o}\right) \times 100,$$

wherein
E—protective effect, %;
P—weight of barium sulphate precipitated after addition of the inhibitor, g;
$P_o$—weight of barium sulphate precipitated without the addition of the inhibitor, g.

Table 3 enlists the data on the protective effect against barium sulphate scaling for the inhibitor prepared by the process according to the present invention (second embodiment), Examples 10 through 14 and for the inhibitors prepared by the processes of the USSR Inventor's Certificates Nos. 726123, 876666 and British Pat. No. 1,479,381.

TABLE 3

| Process for preparing scaling inhibitor according to | Inhibitor concentration in oversaturated solution of barium sulphate (based on phosphonomethylated amines), mg/l | Protective effect % |
|---|---|---|
| 1 | 2 | 3 |
| USSR Inventor's Certificate No. 726123 10.0 | 5.0 | 7 |
| | 13 | |
| | 25.0 | 30 |
| | 50.0 | 43 |
| | 100.0 | 68 |
| USSR Inventor's Certificate | 10.0 | 24 |

TABLE 3-continued

| Process for preparing scaling inhibitor according to | Inhibitor concentration in oversaturated solution of barium sulphate (based on phosphonomethylated amines), mg/l | Protective effect % |
|---|---|---|
| No. 876666 | 50.0 | 30 |
|  | 100.0 | 40 |
| British Patent No. 1,479,381 | 10.0 | 22.7 |
|  | 50.0 | 32.4 |
|  | 100.0 | 39.9 |
| The present invention (second embodiment): |  |  |
| Example 10 | 5.0 | 71 |
|  | 10.0 | 80 |
|  | 25.0 | 90 |
|  | 50.0 | 100 |
|  | 100.0 | 100 |
| Example 11 | 5.0 | 73 |
|  | 10.0 | 88 |
|  | 25.0 | 90 |
|  | 50.0 | 100 |
|  | 100.0 | 100 |
| Example 12 | 5.0 | 75 |
|  | 10.0 | 91 |
|  | 25.0 | 97 |
|  | 50.0 | 100 |
|  | 100.0 | 100 |
| Example 13 | 5.0 | 75 |
|  | 10.0 | 85 |
|  | 25.0 | 93 |
|  | 50.0 | 100 |
|  | 100.0 | 100 |
| Example 14 | 5.0 | 74 |
|  | 10.0 | 32 |
|  | 25.0 | 93 |
|  | 50.0 | 100 |
|  | 100.0 | 100 |

From the data given in the above Table 3 it follows that the inhibitor prepared by the process according to the present invention is considerably superior, in its effectiveness, to the inhibitors prepared by the prior art processes, in inhibiting barium sulphate scaling.

Thus, at the concentration of the inhibitor prepared according to the USSR Inventor's Certificate No. 726123 in an oversaturated solution equal to 25 mg/l the protective effect against barium sulphate scaling is only 30%, while at the same concentration of the inhibitor prepared by the process according to the present invention the protective effect reaches 90%.

What is claimed is:

1. A process for preparing a scaling inhibitor comprising reacting amines selected from the group consisting of 1,3-diaminopropanol-2, polyhydroxypropylenepolyamines of the general formula:

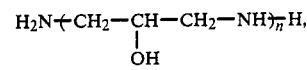

wherein n is 2 to 20, and a mixture of said amines, with formaldehyde and phosphorus trichloride in an aqueous medium at a temperature of from 35° to 50° C.; said formaldehyde and phosphorus trichloride being used in amounts smaller than their respective stoichiometric amounts as calculated for the starting amines.

2. A process for preparing a scaling inhibitor according to claim 1, wherein as the amines a product is used obtained by reacting epichlorohydrin and ammonia as an aqueous solution at a temperature of from 5° to 20° C. and at a molar ratio of the reagents of 1:5–15 respectively, followed by treating the reaction mass with an alkali metal hydroxide employed in an amount of 1.0–1.1 mol per mol of epichlorohydrin and distilling-off the unreacted ammonia; said product having the following composition, percent by mass: a mixture of 1,3-diaminopropanol-2 and polyhydroxypropylenepolyamines of the general formula:

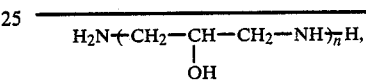

| wherein n = 2–5 | 3 to 33 |
| alkali metal chloride | 2 to 25 |
| water | the balance; | said reaction of the amines with formaldehyde and phosphorus trichloride being effected at a molar ratio thereof equal to 1:2.5–3.3:2.95–3.24 respectively.

3. A process for preparing a scaling inhibitor according to claim 1, wherein as the amines used are amines selected from the group consisting of 1,3-diaminopropanol-2, polyhydroxypropylenepolyamines of the general formula:

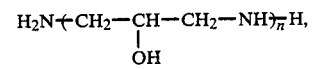

wherein n=2 to 20, and a mixture of said amines; the reaction of the amines with formaldehydes and phosphorus trichloride being carried out at their molar ratio of 1:3.0:3.0 respectively; after reacting said reagents hydrochloric acid contained in the reaction mass is distilled-off therefrom and the reaction mass is neutralized to a pH value of not less than 6.

* * * * *